United States Patent [19]

Kamstra

[11] Patent Number: 4,496,344
[45] Date of Patent: Jan. 29, 1985

[54] MULTIPLE-COMPARTMENT SYRINGE

[75] Inventor: Paulus R. Kamstra, Olst, Netherlands

[73] Assignee: Duphar International Research B.V., Weesp, Netherlands

[21] Appl. No.: 405,366

[22] Filed: Aug. 5, 1982

[30] Foreign Application Priority Data

Aug. 10, 1981 [NL] Netherlands .......................... 8103745

[51] Int. Cl.³ ............................................... A61M 5/00
[52] U.S. Cl. ........................................ 604/90; 604/191
[58] Field of Search .................. 604/89, 90, 82, 187, 604/191, 225, 238; 222/129, 135, 136, 137; 206/528, 538

[56] References Cited

U.S. PATENT DOCUMENTS

| 3,911,916 | 10/1975 | Stevens | 604/191 |
| 3,985,122 | 10/1976 | Topham | 604/191 |
| 4,067,333 | 1/1978 | Reinhardt et al. | 604/191 |
| 4,188,949 | 2/1980 | Antoshkiw | 604/191 |
| 4,235,235 | 11/1980 | Bekkering | 604/238 |
| 4,439,184 | 3/1984 | Wheeler | 604/90 |

Primary Examiner—John D. Yasko
Attorney, Agent, or Firm—Stevens, Davis, Miller & Mosher

[57] ABSTRACT

The invention relates to a syringe for injecting two or more injection liquids which may not be in contact with each other for a longer period of time, comprising a barrel having a piston, a needle on the front side of the barrel, a sealing stopper in the barrel on the front, and one or more separating stoppers which, before use of the syringe, keep the injection liquids separated from each other. The needle is connected to the front of the barrel by means of a needle holder comprising a collar to connect the needle holder to the barrel, an neck to connect the injection needle, and a hollow shaft between collar and neck, in which a passage is formed in the inner wall of the shaft and the rear face of the neck, past which passage the injection liquids can reach the cannula when during use of the syringe the stoppers are moved into the shaft of the needle holder.

6 Claims, 4 Drawing Figures

MULTIPLE-COMPARTMENT SYRINGE

The present invention relates to a multiple-compartment syringe with which two or more different injection liquids which may not be in contact with each other for a longer period of time can be injected sequentially.

The present invention relates in particular to a syringe, comprising a rotationally symmetrical barrel which is open at each end, a piston which is movable in the barrel and seals same and to which a piston rod is or can be connected, a needle or means for the connection thereof to the front end of the barrel, a sealing stopper the dimensions of which are such that it can be provided in a sealing manner in the opening present in the front end of the barrel, one or more separating stoppers to be provided in the barrel and movable therein which can keep the injection liquids present in the barrel separated from each other before use of the syringe in that their circumference sealingly adjoins the inner wall of the barrel, and a finger grip or means for the connection thereof to the outside of the barrel.

Such a syringe is disclosed in U.S. Pat. No. 3,911,916. When using the known syringe, the injection liquids in the barrel can reach the needle via a tube projecting in the barrel and having at least two apertures. In doing this the sharp end of the tube perforates the stopper or stoppers in the barrel. Such a tube having more apertures is difficult to manufacture and to assemble in a barrel of a syringe, so that the manufacturing cost will be high. In this case the significance of the increased manufacturing costs is even greater because syringes previously filled or to be filled in large numbers are preferably manufactured and assembled automatically for the most part and hence large sums of money are involved when the cost of manufacturing one syringe is slightly increased. Another disadvantage of a complicated shape of components, for example, the tube having several apertures, is that these are difficult to clean before assembly, as a result of which the possibility of the presence of small particles in the injection liquid, the so-called "particulate matter" is increased.

However, a more serious disadvantage of the syringe described in the above-mentioned United States Patent is that during use the stopper or stoppers have to be perforated by the sharp end of the tube. It is almost inevitable that rubber particles of the stopper or stoppers will contaminate the injection liquid and may enter the body of the patient. There is also a fair chance that cut particles of rubber will clog the tube, as a result of which the syringe can no longer be used at all.

The above-mentioned disadvantages are obviated by the two-compartment syringe shown in FIG. 1 of Netherlands Patent Application 7409809. In this syringe, the injection liquid present behind the stopper can reach the cannula via a by-pass in the wall of the barrel. Such a two-compartment syringe is suitable for the desired purpose, namely the injection of two different injection liquids which are not compatible with each other for a longer period of time. However, this two-compartment syringe cannot be used for more than two injection liquids. In fact, in that case quite a different barrel, no doubt the most important component of the syringe described, would have to be used, namely a barrel having a by-pass which is slightly longer than the collective stoppers. Only then can the rearmost injection liquid, namely that between the rear stopper and the piston, also be injected via the by-pass. In other words, the above-described syringe is actually suitable only as a two-compartment syringe and cannot be universally used as a multiple-compartment syringe without fundamental changes. Another disadvantage of the syringe shown in the aboveidentified Netherlands patent application is the absence of a means to ensure the flow of the injection liquid from the by-pass to the cannula. As a result of fact, the possibility exists that during the injection the stopper will clog the entrance to the cannula.

Syringes comparable to the two-compartment syringe shown in the above-mentioned Netherlands patent application are described in U.S. Pat. Nos. 2,717,601, and 3,330,282, and in German patent application (Auslegeschrift) 1,105,113. However, these syringes are not destined for injecting two injection liquids to be stored separately, but comprise a medicament in the solid state and separated therefrom a solvent for said medicament. So when such a syringe is used, the medicament must first be dissolved before the injection can be administered. The construction of the syringes described in the last-mentioned U.S. patents and German patent application moreover has the same disadvantage as stated for the syringe known from Netherlands patent application 7409809, namely that these syringes cannot be universally used for multiple-compartment syringes.

It is an object of the present invention to provide a multiple-compartment syringe which can be universally used, i.e. can be used without fundamental changes both for two and for more than two different injection liquids, and which is of simple construction so that the manufacturing cost can be kept low. This object can be achieved with a syringe of the kind mentioned in the opening paragraph which is characterized according to the present invention in that the needle is or can be connected to the front of the barrel by means of a needle holder consisting of a collar which is or can be connected sealingly to the front of the barrel, a neck in which the injection needle is or can be connected, and a hollow shaft between collar and neck, in which a passage is formed in the inner wall of the shaft and the rear face of the neck, past which passage the injection liquids can reach the cannula when during use of the syringe the stoppers are moved into the shaft of the needle holder. If desired, the number of different medicaments in the barrel of the syringe can easily be varied by providing more or fewer separating stoppers in the barrel. Only the needle holder should be adapted to the number of stoppers. In fact, the length of the inner wall of the shaft should be slightly greater than the overall length of the collective stoppers, that is to say separating stopper or stoppers and sealing stopper collectively, so that the rearmost injection liquid, i.e. that between the rear stopper and the piston, can still reach the cannula without obstructions.

In a favourable embodiment of the present invention the rear face of the needle holder comprises a few spacing supports and the space bounded by the inner wall of the shaft and the spacing supports on the rear face of the neck has the same or a slightly larger circumference than the inner wall of the barrel and is slightly longer than the collective stoppers so that in the extreme forward position the collective stoppers can fill said space substantially entirely, in which, however, an opening or openings remain(s) between the stoppers and the inner wall which extend(s) to a point behind the stoppers. In another favourable embodiment, the front face of the sealing stopper comprises a few spacing supports and the space bounded by the inner wall of the shaft and the rear face of the neck of the needle holder has the same or a slightly larger circumference than the inner wall of the barrel and is slightly longer than the collective stoppers, including the spacing supports on the sealing stopper, so that in the extreme forward position the collective stoppers can fill said space substantially entirely, in which, however, an opening or openings remain(s) between the stoppers and the inner wall of the shaft which extend(s) to a point behind the stoppers.

In still another favourable embodiment of the present invention, one or more slots extending from the rear end of the shaft to the rear aperture of the cannula are recessed in the inner wall of the shaft and the rear face of the neck of the needle holder, and the inner wall of the shaft, apart from the slot or slots, is slightly longer than the collective stoppers so that the collective stoppers in the extreme forward position do not cover the end of the slot or slots adjoining the barrel. A needle holder having such a by-pass or by-passes is described and shown in Netherlands patent application No. 7714308 in the name of Applicants. This known needle holder, however, is destined for a mono-compartment syringe so that the shaft is suitable only for receiving one stopper. The needle holder for the multiple-compartment syringe of the present invention, however, has a shaft length adapted to the desired number of stoppers, which means that the inner wall of the shaft is slightly longer than the length of the collective stoppers. Only in this manner can the last injection liquid, that is to say the injection liquid between the rear separating stopper and the piston, reach the cannula.

It will be obvious that the present invention also relates to a prefilled syringe, that is to say a syringe filled with different injection liquids.

The multiple-compartment syringe according to the present invention is particularly suitable for a bipartite construction. The first part is formed by the barrel with injection liquids, in which the stoppers and the piston are provided, and which, if desired, comprises a finger grip and/or a piston rod. The second part of the syringe is formed by the needle holder with the injection needle connected thereto. The shaft length of the needle holder is adapted to the length of the stoppers and the number of stoppers (hence the number of different injection liquids) in the barrel. When the number of injection liquids is varied, a needle holder having a different shaft length may be used.

This bipartite construction has the advantages described in the above-mentioned Netherlands patent application. It is possible, for example, to provide the user separately with a needle holder and with needles of different dimensions so that he can choose the correct needle for each individual case. The barrel with medicament also supplied separately is the only part of the syringe which (often) is restricted to an expiration term and/or must be subjected to a special treatment, for example, post-sterilization, storage in the dark and/or while cooling. This not only has advantages from a technical point of view of production, but is also of importance for a more economical method of manufacturing the syringes.

In this bipartite construction the needle holder can be connected to the barrel in a simple manner, for example by pressing the needle holder on the barrel (snap-cap construction), or, in the case of a screw or bayonet lock, by screwing. In this embodiment the syringe can also be packaged more easily, because the separate parts have a smaller length. In addition the sterilization of these separate parts is simpler, while also the expensive assembly in a sterile room can be reduced by one treatment. Of course, the diameter and the connection means of the needle holder and the barrel should be matched to each other.

BRIEF DESCRIPTION OF THE DRAWING

The present invention will now be described in greater detail with reference to the preferred embodiments shown in the accompanying drawing, in which.

Figure 1:
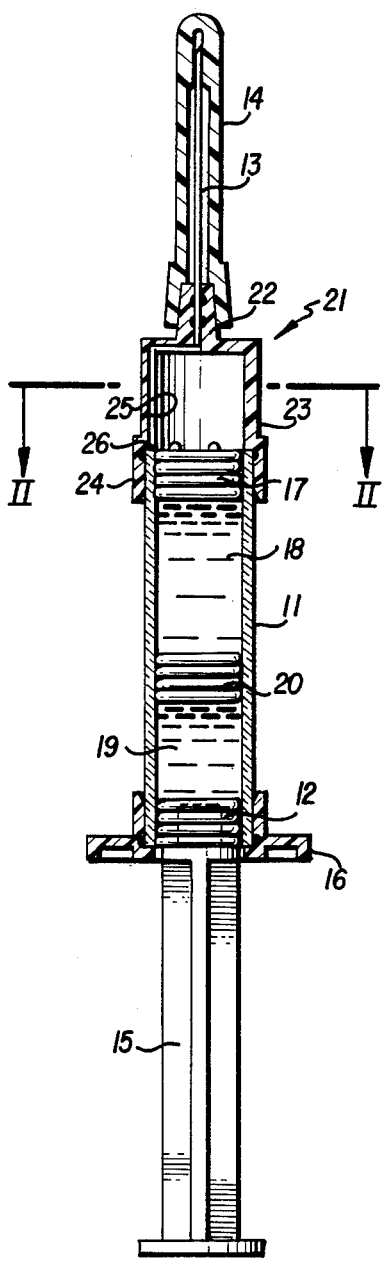
FIG. 1 is a longitudinal sectional view of a syringe according to the present invention in a condition in which it can be transported and stored.
Figure 2:
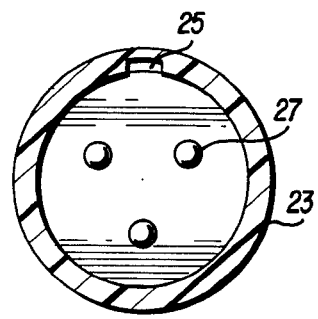
FIG. 2 is a sectional view through the needle holder of the syringe shown in FIG. 1 taken on the line II—II in FIG. 1 and viewed in the direction of the stopper.

The syringe shown in FIGS. 1 and 2 comprises a barrel 11 in which a piston 12 is provided at one end while the other end comprises an injection needle 13 having a protective sheath (guard) 14. The piston can be moved by means of a piston rod 15 which can be connected to the piston, for example, by means of a screwing operation. At the same end where the piston is present, the barrel comprises a finger grip 16 connected to the barrel according to the so-called snap-cap principle. Another equally reliable connection is described in British Patent Specification 1479536 in the name of Applicants; the finger grip described in this Specification consists of a tensioning collet which can be clamped around the end of the barrel by means of a tensioning sheath. The finger grip preferably consists of a somewhat resilient material, for example a plastic material. The barrel is manufactured from rigid material, preferably glass. In another embodiment, the finger grip is a radially projecting flange-shaped part of the syringe. Of course, other constructions known to those skilled in the art are possible.

A stopper 17 sealing the barrel is present in the end of the barrel remote from the piston. Two different injection liquids 18 and 19 are present in the barrel between the piston 12 and stopper 17. These injection liquids are kept separated from each other by a separating stopper 20. The piston and the stoppers are manufactured from resilient material, preferably rubber of a pharmaceutical quality.

The injection needle 13 is connected to the barrel by means of a needle holder 21. The needle holder consists of a neck 22 which keeps the needle clamped, a shaft 23 and a collar 24. The needle holder is preferably manufactured from slightly resilient material which, however, is sufficiently resistant to deformation, for example, plastic, and is connected to the end of the barrel by means of a snap-cap construction. In another embodiment of the present invention the needle holder may be connected to the barrel by means of a screw or bayonet connection or, when the barrel also comprises a collar, by means of a clamping ring. One or more slots 25 are recessed in the inner wall of the shaft and the rear face of the neck, which slots extend into the rear end of the cannula. The dimensions of the slot or slots should be such that the injection liquids can pass through sufficiently easily; this is achieved by making the diameter of the slot or the overall cross-section of the slots collectively at least as large as that of the cannula. The shaft of the needle holder is constructed so that when the sealing stopper 17 is axially moved forward it is received by the shaft in a sliding manner. Therefore, the inner wall of the shaft has the same or a slightly larger circumference than the inner wall of the barrel. It is desired that the sealing stopper should remain in a sealing position in the shaft when during the so-called nurse-aspiration the piston is slightly retracted. Therefore, the shaft, apart from the slot or slots, preferably has a somewhat oval cross-section in which the shortest diameter is slightly smaller than the inside diameter of the barrel. Measured internally the shaft of the needle holder is slightly longer than the overall length of the stoppers 17 and 20 collectively, so that the portion 26 of the slot or slots adjoining the barrel is free when the two plugs have been moved forward entirely against the rear face of the neck of the needle holder.

When using the syringe according to the present invention, the piston 12 is pushed forward by means of the piston rod 15. The pressure exerted on the piston propagates to the stopper 17 via the liquid columns 18 and 19 and the stopper 20. When the stopper has been moved in the shaft to a point beyond the portion 26 of the slot or slots adjoining the barrel, the injection liquid 18 present behind said stopper can pass said stopper and so reach the cannula. When the front of the separating stopper 20 touches the rear of the sealing stopper 17, both stoppers are collectively moved farther forward under the influence of the forward movement of the piston. In the extreme forward position of the stoppers, in which the front of stopper 17 touches the rear face of the neck 22 of the needle holder, the end 26 of the slot or slots adjoining the barrel has just become uncovered so that under the influence of the forward movement of the piston, injection liquid 19 can be injected as completely as possible. It will be feasible that the front of the separating stopper and the rear of the sealing stopper, as well as the front of the piston and the rear of the separating stopper, are complementary and preferably flat surfaces so as to keep the residual volume of injection liquids as small as possible. For the same reason, the front of the sealing stopper and the rear face of the neck of the needle holder are shaped so that in the extreme forward position of the sealing stopper the space between the front of the stopper and the entrance to the cannula is as small as possible.

Figure 3:
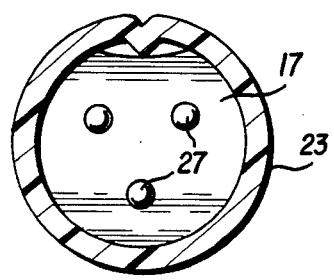
FIGS. 3 and 4 are cross-sectional views through the needle holder of the syringe taken on the same line as shown in FIG. 1, but this time of other embodiments of the syringe according to the invention.
Figure 4:
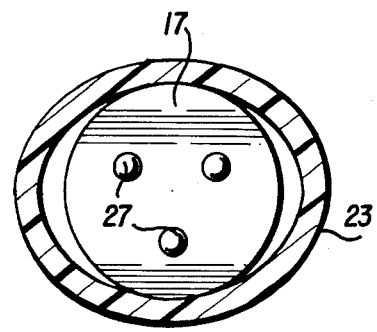

In another favourable embodiment of the present invention the inner wall of the shaft of the needle holder does not comprise one or more slots, but rather comprises a ridge extending in the longitudinal direction of the shaft; FIG. 3 is a cross-sectional view of a needle holder in this embodiment. In still another embodiment, the inner wall of the shaft of the needle holder has an oval cross-section, as is shown in FIG. 4. In still another embodiment, not shown in the figures, the inner wall of the shaft of the needle holder has a circular cross-section, and has a slightly larger diameter than the expanded stoppers, so that the injection liquid can easily pass the stoppers. In order not to obstruct the entrance of the injection liquid to the cannula, the rear face of the neck of the needle holder or the front face of the sealing stopper in these embodiments includes spacing supports, for example, three projections. The cross-sectional views of FIGS. 3 and 4 are viewed in the direction of the sealing stopper and are taken at the instant when the sealing stopper is moved into the shaft of the needle holder. The front of the sealing stopper 17 has three projections 27 in the form of caps or truncated cones. As shown in FIG. 3, ducts have been formed on either side of the ridge through which the injection liquids can pass the stoppers; in the FIG. 4 embodiment openings are also formed through which the injection liquids can enter the cannula.

In another embodiment of the present invention the syringe does not have a needle in the position in which the syringe is stored, but has a needle connection means. When such a syringe is used, the needle is placed on the neck of the needle holder by means of a needle cone, for example, a so-called Luer cone, after the protection cap has been removed. In this embodiment, the opening in the neck of the needle holder is closed on the outside by means of a protective cap which ensures the sterility of that part of the needle holder and hence the interior of the syringe.

I claim:

1. A syringe for injecting two or more different injection liquids which may not be in contact with each other for a long period of time, comprising:
  a rotationally symmetrical barrel which is open at each end, to which barrel a finger grip means is connectable;
  a piston which is movable in the barrel and seals same, to which piston a piston rod is connectable;
  a needle or means to connect same to the front end of the barrel;
  a sealing stopper, the dimensions of which are such that it can be provided sealingly in the opening on the front end of the barrel;
  at least one separating stopper to be provided in the barrel and movable therein, said stopper having a circumference that sealingly adjoins the inner wall of the barrel, thereby keeping the injection liquids present in the barrel separated from each other prior to use of the syringe; and
  a needle holder comprising a collar which is sealingly engageable with the front end of the barrel; a neck for sealable attachment to an injection needle; a hollow shaft between the collar and the neck; a plurality of spacing supports included in the rear face of the neck; and a passage formed in the inner wall of the shaft and the rear face of the neck, said syringe being characterized in that the space bounded by the inner wall of the shaft and the spacing supports on the rear face of the neck has the same or a slightly larger circumference than the circumference of the inner wall of the barrel and is slightly longer than the length of the collective stoppers, so that in the extreme forward position the collective stoppers can substantially entirely fill said space, in which however at least one opening remains between the stoppers and the inner wall of the shaft, said opening extending to a point behind the stoppers.

2. A syringe for injecting two or more different injection liquids which may not be in contact with each other for a long period of time, comprising:
  a rotationally symmetrical barrel which is open at each end, to which barrel a finger grip means is connectable;
  a piston which is movable in the barrel and seals same, to which piston a piston rod is connectable;
  a needle or means to connect same to the front end of the barrel;

a sealing stopper, the dimensions of which are such that it can be provided sealingly in the opening on the front end of the barrel;

at least one separating stopper to be provided in the barrel and movable therein, said stopper having a circumference that sealingly adjoins the inner wall of the barrel, thereby keeping the injection liquids present in the barrel separated from each other prior to use of the syringe; and a needle holder comprising a collar which is sealingly engageable with the front end of the barrel; a neck for sealable attachment to an injection needle; a hollow shaft between the collar and the neck; a plurality of spacing supports included in the front face of the sealing stopper; and a passage formed in the inner wall of the shaft and the rear face of the neck, said syringe being characterized in that the space bounded by the inner wall of the shaft and the rear face of the neck of the needle holder has a slightly larger circumference than the circumference of the inner wall of the barrel and is slightly longer than the length of the collective stoppers, including the spacing supports on the sealing stopper, so that in the extreme forward position the collective stoppers can substantially entirely fill said space, in which however at least one opening remains between the stoppers and the inner wall of the shaft, said opening extending to a point behind the stoppers.

3. A syringe for injecting two or more different injection liquids which may not be in contact with each other for a long period of time, comprising:

a rotationally symmetrical barrel which is open at each end, to which barrel a finger grip means is connectable;

a piston which is movable in the barrel and seals same, to which piston a piston rod is connectable;

a needle or means to connect same to the front end of the barrel;

a sealing stopper, the dimensions of which are such that it can be provided sealingly in the opening on the front end of the barrel;

at least one separating stopper to be provided in the barrel and movable therein, said stopper having a circumference that sealingly adjoins the inner wall of the barrel, thereby keeping the injection liquids present in the barrel separated from each other prior to use of the syringe; and a needle holder comprising a collar which is sealingly engageable with the front end of the barrel; a neck for sealable attachment to an injection needle; a hollow shaft between the collar and the neck; and a passage formed in the inner wall of the shaft and the rear face of the neck, said passage comprising at least one slot extending from the rear end of the shaft to the rear aperture of the needle, said slot being recessed in the inner wall of the shaft and the rear face of the neck of the needle holder, said syringe being characterized in that the space bounded by the inner wall of the shaft and the rear face of the neck, apart from said slot, has approximately the same circumference as the inner wall of the barrel and is slightly longer than the length of the collective stoppers so that the collective stoppers, in the extreme forward position, do not cover a portion of said slot adjoining the barrel.

4. A syringe as claimed in claims 1, 2 or 3, characterized in that the barrel is filled with different injection liquids which are present between the piston and the separating stopper, between the separating stopper and the sealing stopper, and if more than one separating stopper is present, between the separating stoppers, the front end of the barrel being sealed by the sealing stopper which is present just rearwardly of the front end of the barrel, the front face of the stopper being substantially in line with the front end of the barrel.

5. A syringe as claimed in claims 4, 1, 2 or 3, said syringe comprising a needle holder provided with an injection needle; and a separate barrel to be connected to the needle holder, said barrel including a piston, a piston rod connected to said piston, at least two stoppers, and a finger grip attached to the exterior of the barrel.

6. A needle holder for a syringe comprising a collar with which the needle holder can be sealingly connected to the front of a barrel in which a piston and at least two stoppers can be provided, a neck in which an injection needle can be connected, and a hollow shaft connecting the collar to the neck in a sealing manner, characterized in that the space bounded by the inner wall of the shaft and the rear face of the neck is slightly longer than the length of the collective stoppers to be provided in the barrel and has a slightly larger circumference than the inner wall of the barrel.

* * * * *